US00PP09833P

United States Patent [19]

Marciel et al.

[11] Patent Number: Plant 9,833

[45] Date of Patent: Mar. 25, 1997

[54] HYBRID TEA ROSE VARIETY NAMED 'DEVCAL'

[75] Inventors: Stanley G. Marciel; Jeanne A. Marciel, both of Aptos, Calif.

[73] Assignee: DeVor Nurseries, Inc., Watsonville, Calif.

[21] Appl. No.: 415,172

[22] Filed: Mar. 31, 1995

[51] Int. Cl.[6] ..... A01H 5/00

[52] U.S. Cl. ..... Plt./14

[58] Field of Search ..... Plt./14, 11

*Primary Examiner*—Howard J. Locker

*Attorney, Agent, or Firm*—Christie, Parker & Hale, LLP

[57] ABSTRACT

A hybrid tea rose variety producing white flowers.

1 Drawing Sheet

SUMMARY OF THE INVENTION

The present invention relates to a new and distinct hybrid tea red variety which was originated by my crossing as seed and pollen parents two unnamed and undistributed seedlings of our creation, Nos. 64022-39 and 77243-1, respectively. The new variety grows more vigorously than either of its parents, flowers are larger and foliage is deeper green. The varietal denomination of this new rose is 'Devcal'.

Among the novel characteristics possessed by this new variety which distinguish it from its parents and all other varieties of which I am aware are its attractive white flowers borne on a plant with deep green foliage.

Asexual reproduction by budding of the new variety as performed in Watsonville, Calif., shows that the foregoing and other distinguishing characteristics come true to form and are established and transmitted through succeeding propagations. Other known useful forms of asexual reproduction may be also employed.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Hybrid tea.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small, about 1⅛ inch long by about ½ inch wide.

(2) *Form.*—Urn shape.

(3) *Color.*—When sepals first divide, bud color is near 155A.

(4) *Sepals.*—Longer than bud, about 3 cm to 3.5 cm long, spread and reflex when bloom opens; some sepals are foliaceous with leaf-shaped ends. Color: Near 144A.

(5) *Peduncle.*—Length: About 5 to about 6 cm. Aspect: Smooth. Strength: Erect, sturdy. Color: Near 144C.

(6) *Bracts.*—Occasional.

B. Bloom:

(1) *Size.*—Average size when fully expanded — about 7 cm to about 9 cm.

(2) *Borne.*—Singly.

(3) *Form.*—Imbricated, outer petals quill to points and inner petals roll under.

(4) *Petalage.*—Number of petals under normal conditions — about 40 to 50.

(5) *Color (⅓ to ½ open).*—Outer petals — Top Surface: near 155B with base & apex near 157C; Undersurface: near 157C. Inner Petals — Top Surface: near 155B with base near 157C; Undersurface: near 157B. Base of petals (point of attachment): Near 157C. General tonality from a distance: White.

(6) *Color (fully open).*—Outer petals — Top surface: near 155C with base near 157C; Undersurface: near 155C. Inner petals — Top surface: near 155C with base near 157B; Undersurface: near 155C with base near 157C. Base of petals (point of attachment): Near 2C. General tonality from a distance: White.

(7) *Color change.*—As bloom ages: Color remains as fully opened blooms. Petal top surface: Same as fully opened. Petal undersurface: Same as fully opened. Petals: (1) Texture: Thick, smooth. (2) Appearance: Matte inside and outside. (3) Form: Elliptic with pointed tip. (4) Arrangement: Imbricated. (5) Petaloids: Many. (6) Fragrance: None. (7) Lasting quality: On plant about 6 to 10 days, after cutting about 7 to 9 days. (8) Persistence: Petals drop off cleanly.

REPRODUCTIVE ORGANS

A. Stamens:

(1) *Arrangement.*—Irregularly arranged around styles.

(2) *Anthers.*—Color near 20B.

(3) *Filaments.*—Near 1C.

(4) *Pollen.*—Color — near 20B.

B. Pistils:

(1) *Styles.*—Bunched, uneven.

(2) *Stigmas.*—Color near 33A, tips near 11C.

C. Characteristics of hips: Not observed.

PLANT

A. Form: Upright.

B. Growth: Very vigorous; about 106 cm to about 130 cm in height at first season.

C. Foliage: Compound 3 and 5 leaflets.

(1) *Size.*—Medium.

(2) *Quantity.*—Abundant.

(3) *Color.*—New foliage — upper side near 146A underside near 147B; mature foliage — upper side near 147A, underside near 147B.

(4) *Shape.*—Oval.

(5) *Texture.*—Upper side glossy, leathery smooth; underside leathery, smooth.

(6) *Edge.*—Serrated.

(7) *Serration.*—Denticulate.

(8) *Leaf stem.*—Color — medium green.

(9) *Stipules.*—Medium, slightly bearded, adnate and parallel.

(10) *Rachis.*—Small prickles on underside.

(11) *Petioles.*—Top near 146B, underside near 146C.

(12) *Auricle.*—Thin, slightly glandular.

(13) *Resistance to disease.*—Very resistant to black-spot, mildew and rust.

D. Wood:

(1) *New wood.*—Color near 146C, bark smooth.

(2) *Old wood.*—Color near 146A, bark smooth.

E. Flower stem: About 11 cm to about 23 cm from last cut.

F. Thorns:

(1) *Thorns.*—Quantity: On main stalk, some; laterals from stalk, some. Form: Slightly curved downward. Length: Medium. Color: Near 144C (when young). Position: Irregular.

(2) *Prickles.*—None.

G. Winter hardiness: Winter hardy in Watsonville, Calif.

We claim:

1. A new and distinct hybrid tea rose plant variety, substantially as shown and described.

* * * * *

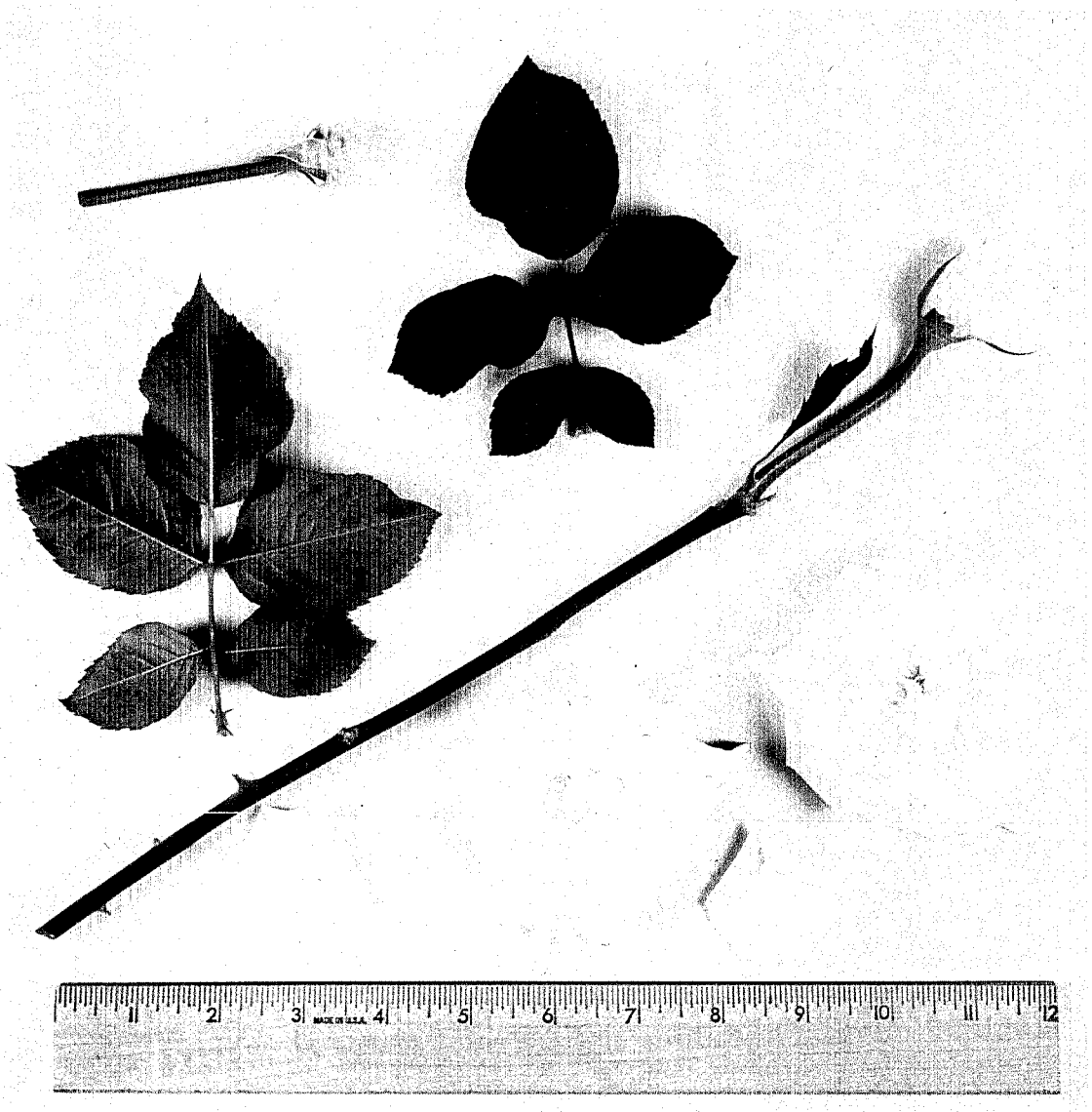
1
2
3
4
5
6
7
8
9
10
11
12